| United States Patent [19] | [11] Patent Number: 4,940,704 |
|---|---|
| Effland et al. | [45] Date of Patent: Jul. 10, 1990 |

[54] PYRIDO[3,4-B][1,4]BENZOXAZEPINES

[75] Inventors: Richard C. Effland; Joseph T. Klein, both of Bridgewater, N.J.

[73] Assignee: Hoechst-Roussel Pharmaceutical Inc., Somerville, N.J.

[21] Appl. No.: 394,613

[22] Filed: Aug. 16, 1989

[51] Int. Cl.$^5$ .................... C07D 498/04; A61K 31/55
[52] U.S. Cl. .................................. 514/211; 540/488; 540/548
[58] Field of Search ................ 540/488, 548; 514/211

[56] References Cited

U.S. PATENT DOCUMENTS

| 3,123,614 | 3/1964 | Yale et al. | 540/548 |
|---|---|---|---|
| 3,450,684 | 6/1969 | Sweet et al. | 540/488 |
| 3,459,737 | 8/1969 | Schmidt | 540/488 |
| 3,849,424 | 11/1974 | Yale | 540/547 |

FOREIGN PATENT DOCUMENTS 5315 9/1967 France .............................. 540/488

OTHER PUBLICATIONS

K. Rajyalakshmi and V. R. Srinivasan, Chem. Abs., 92, 110978g (1980).
K. Thomae, Chem. Abs., 66, 65542k (1967).
Brewster et al., "J. Het. Chem.", vol. 15, pp. 1497–1499 (1978).

*Primary Examiner*—Robert T. Bond
*Attorney, Agent, or Firm*—Raymond R. Wittekind

[57] ABSTRACT

Novel pyrido[3,4-b][1,4]benzoxazepines, intermediates for the preparation thereof, and methods for treating depression, alleviating pain, and relieving memory dysfunction are disclosed.

26 Claims, No Drawings

PYRIDO[3,4-B][1,4]BENZOXAZEPINES

The present invention relates to benzoxazepines. More particularly, the present invention relates to pyrido[3,4-b][1,4]benzoxazepines of the formula

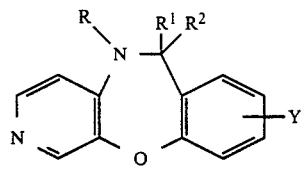

wherein R is hydrogen, alkyl, alkanoyl, a group of the formula $(CH_2)_m NR^3 R^4$ wherein $R^3$ and $R^4$ are alkyl and m is 2 or 3, a group of the formula $CH_2C\equiv CH$, a group of the formula

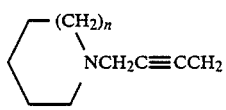

wherein n is 0 or 1; $R^1$ and $R^2$ are hydrogen; $R^1$ and $R^2$ taken together with the carbon atom to which they are attached form a group of the formula C=O, Y is hydrogen, alkyl, halogen, alkoxy, or trifluoromethyl; an optical isomer thereof; or a pharmaceutically acceptable salt thereof, which are useful for treating depression, alleviating pain, and relieving memory dysfunction, for example, memory dysfunction such as that associated with reduced cholinergic function in Alzheimer's disease, alone or in combination with adjuvants.

Subgeneric to the pyrido[3,4-b][1,4-benzoxazepines of the present invention are compounds wherein (a) $R^1$ and $R^2$ are hydrogen and (b) $R^1$ and $R^2$ taken together with the carbon atom to which they are attached form a group of the formula C=O.

The present invention also relates to 6-(4-methyl-1-piperazinyl)pyrido[3,4-b]-[1,4]benzoxazepine of the formula

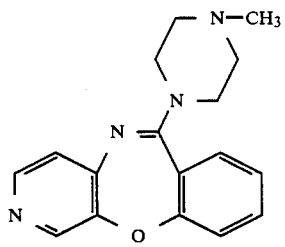

As used throughout the specification and appended claims, the term "alkyl" refers to a straight or branched chain hydrocarbon radical containing no unsaturation and having 1 to 10 carbon atoms such as methyl, ethyl, n-propyl, tert-butyl, hexyl, octyl, decyl and the like; the term "alkoxy" refers to a monovalent substituent which consists of an alkyl group linked through an ether oxygen and having its free valence bond from the ether oxygen such as methoxy, ethoxy, isopropoxy, tert-butoxy, heroxy, octoxy, decoxy and the like; The term "alkanoic acid" refers to a compound formed by combination of a carboxyl group with a hydrogen atom or alkyl group. Examples of alkanoic acids are formic acid, acetic acid, propanoic acid, 2-methylpropionic acid, hexanoic acid, octanoic acid, decanoic acid and the like; the term "alkanoyl" refers to a radical form by removal of the hydroxyl group of an alkanoic acid. Examples of alkanoyl radicals are acetyl, propionyl, 2-methylpropionyl, hexanoyl, ocatanoyl, decanoyl and the like; the term "halogen" refers to a member of the family fluorine, chlorine, bromine or iodine. The term "lower" as applied to any of the aforementioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, or by synthesis from optically active precursors.

The present invention comprehends all optical isomers and racemic forms thereof of the compounds disclosed and claimed herein and the formulas of the compounds shown herein are intended to encompass all possible optical isomers of the compounds so depicted.

The novel pyridobenzoxazepines of the present invention are synthesized by the processes illustrated in the Reaction Scheme.

To gain entry into the basic pyridobenzoxazepine system, i.e., to elaborate a pyridobenzoxazepine 4, an (aminopyridyloxy)benzoic acid ester 1, the preparation of which is described in U.S. patent application Docket No. HR 1164, is cyclized to a pyridobenzoxazepione 2 which is reduced to a benzoxazepine 4.

The cyclization is performed by contacting an (aminopyridyloxy)benzoic acid ester 1 wherein $R^5$ is alkyl with a base such as, for example, an alkali metal hydride (lithium hydride, potassium hydride, or sodium hydride) in a dipolar aprotic solvent such as, for example, dimethylacetamide, dimethylformamide, dimethylsulfoxide, or hexamethylphosphoramide. Sodium hydride and dimethylformamide are preferred. The cyclization temperature is not narrowly critical; however, it is preferred to perform the reaction at about ambient temperature.

The reduction of pyridobenzoxazepinone 2 to pyridobenzoxazepine 4 is effected by an alkali metal hydride, for example, lithium aluminum hydride in an ethereal solvent, for example, tetrahydrofuran at about ambient temperature.

To introduce a substituent on the nitrogen atom of the oxazepinone moiety, i.e., to prepare a pyridobenzoxazepinone 3 wherein $R^6$ is alkyl, a group of the formula $(CH_2)_m NR^3 R^4$ wherein $R^3$, $R^4$ and m are as hereinbeforementioned, or a group of the formula $CH_2C\equiv CH$, an oxazepinone 2 is alkylated with a compound of formula 7

$$(R^6)_2SO_4 \qquad\qquad 7$$

wherein $R^6$ is alkyl or a compound of formula 8

$$R^6 Hal \qquad\qquad 8$$

wherein $R^6$ is a group of the formula $(CH_2)_m NR^3 R^4$ wherein $R^3$, $R^4$ and m are as above, or a group of the formula $CH_2C\equiv CH$, Hal is chloro or bromo, in a dipolar aprotic solvent (e.g. dimethylacetamide, dimethylformamide, dimethylsulfoxide or hexamethylphosphoramide) in the presence of an alkali metal hydride (e.g., sodium hydride or potassium hydride) at a temperature within the range of about −20° to about 100° C. Dimethylformamide in the preferred solvent and sodium hydride is the preferred alkali metal hydride. An alkylation temperature of about 0° to about 80° C. is preferred.

Similarly, an oxazepine 4 is alkylated, for example, to an N-alkyloxazepine 5 (wherein $R^6$ is alkyl) by means of a dialkylsulfate of formul 7 wherein $R^6$ is alkyl in the presence of sodium hydride in dimethylformamide at about 0° C.

To prepared an N-acyloxazepine 5 wherein $R^6$ is alkanoyl, an oxazepine 4 is condensed, for example, with an anhydride 9

   $(R^7O)_2CO$   9 wherein $R^7$ is alkyl to provide 5. The condensation is conducted in the presence of a base such as an alkali metal carboante (e.g., sodium carbonate or potassium carbonate), preferably in the presence of sodium carbonate at about ambient temperature.

To complete the synthesis of pyridobenzoxazepinones 3 wherein $R^6$ is a group of the formula

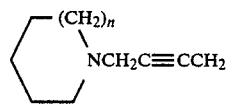

wherein n is 0 or 1, one treats an oxazepinone 3 wherein $R^6$ is a group of the formula $CH_2C\equiv CH$ with a tertiary amine of formula 10

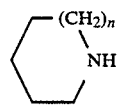   10 wherein n is as above and formaldehyde, preferably in the form of paraformaldehyde, in an ethereal solvent such as, for example, tetrahydrofuran, dioxane, dimethoxyethane, or 2-methoxyethyl ether, preferably dioxane, at a reaction temperature within the range of about 75° to about 120° C., preferably at about 100° C. A promoter such as cuprous bromide or cuprous chloride may be employed to facilitate the reaction. 6-(4-Alkyl-1-piperazinyl)pyrido[3,4-b][1,4]benzoxazepines 6 wherein $R^7$ is alkyl are prepared by treating an oxazepinone 2 with a phosphorous trihaldie, phosphorus pentahalide, or a phosphorous oxyhalide, a phosphorous oxyhalide such as phosphorous oxychloride being preferred, followed by an N-alkylpiperazine of formula 11

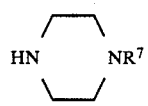   11 wherein $R^7$ is alkyl in an aromatic solvent such as benzene, toluene, or xylene, toluene being preferred, at or within the range of about 60° to 100° C., a reaction temperature of about 80° C. being preferred.

The pyridobenzoxazepines of the present invention are useful in the treatment of depression in mammals, as demonstrated by their ability to inhibit tetrabenazine-induced depression in mice [International Journal of Neuropharmacology 8, 73 (1969)], a standard assay for the determination of antidepressant properties. This, for instance, the intraperitoneal dose at which 6-(4-methyl-1-piperazinyl)pyrido[3,4-b][1,4]benzoxazepine effects a 50% inhibition of tetrabenazine-induced ptosis ($ED_{50}$) in mice is 11.1 mg/kg of body weight and the intraperitoneal dose at which 5-(2-dimethylaminoethyl-pyrido[3,4-b][1,4]benzoxazepin-6(5H)-one effects a 40% inhibition of tetrabenazine-induced ptosis in mice is 20 mg/kg of body weight. Amitriptyline, a standard antidepressant, exhibits an $ED_{50}$ of 1.5, intraperitoneally, in this assay.

Antidepressant response is achieved when the present pyridobenzoxazepines are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they they do not, to any extent, limit the scope or practice of the invention.

The pyridobenzoxazepines of the present invention are useful an analgetic agents due to their ability to alleviate pain in mammals. The analgetic utility of compounds of this invention is demonstrated in the phenyl-p-quinone writhing assay in mice, a standard assay for analgesia [Proc. Soc. Exptl. Bio. Med. 95, 729 (1957)]. Thus, for example, the subcutaneous dos effecting a 63% inhibition of writhing in mice in this assay is 20 mg/kg of body weight for 5-methylpyrido[3,4-b][1,4]benzoxazepin-6(5H)-one, the subcutaneous dose effecting a 31% inhibition of writhing is 20 mg/kg of body weight for 5,6-dihydro-5-methylpyrido[3,4-b][1,4]benzoxazepine and the subcutaneous dose effecting a calculated 50% inhibition of writhing in mice in this assay is 19.6 mg/kg if body weight for 5-acetyl-5,6-dihydropyrido[3,4- ][1,4]benzoxazepine and 13.5 mg/kg of body weight for 6-(4-methyl-1-piperazinyl)-pyrido[3,4-b][1,4 benzoxazepine, respectively. Propoxyphene, a standard analgetic, exhibits a calculated 50% inhibition of writhing at 3.9 mg/kg of body weight by subcutaneous administration in this assay.

Analgetic production is achieved when the present pyridobenzoxazepines are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they they do not, to any extent, limit the scope or practice of the invention.

The pyridobenzoxazepines of the present invention are useful as agents for the relief of memory dysfunction, particularly dysfunctions associated with decreased cholinergic activity such as those found in Alzheimer's disease. Relief of memory dysfunction activity of the instant compounds is demonstrated in the dark avoidance assay, an assay for the determination of the reversal of the effects of scopolamine induced memory deficits associated with decreased levels of acetylcholine in the brain. In this assay, three groups of 15 male CFW mice were used—a vehicle/vehicle control group, a scopolamine/vehicle group, and a scopolamine/drug group. Thirty minutes prior to training, the vehicle/vehicle control group received normal saline subcutaneously, and the scopolamine/vehicle and scopolamine/drug groups received scopolamine subcutaneously (3.0 mg/kg, administered as scopolamine hydrobromide). Five minutes prior to training, the vehicle/vehicle control and scopolamine/vehicle groups received distilled water and the scopolamine/drug group received the test compound in distilled water.

The training/testing apparatus consisted of a plexiglass box approximately 48 cm long, 30 cm high and tapering from 26 cm wide at the top to 3 cm wide at the bottom. The interior of the box was divided equally by a vertical barrier into a light compartment (illuminated by a 25-watt reflector lamp suspended 30 cm from the floor) and a dark compartment (covered). There was a hole at the bottom of the barrier 2.5 cm wide and 6 cm tall and a trap door which could be dropped to prevent an animal from passing between the two compartments. A Coulbourn Instruments small animal shocker was attached to two metal plates which ran the entire length of the apparatus, and a photocell was placed in the dark compartment 7.5 cm from the vertical barrier and 2 cm off the floor. The behavioral session was controlled by PDP 11/34 minicomputer.

At the end of the pretreatment interval, an animal was place in the light chamber directly under the light fixture, facing away from the door to the dark chamber. The apparatus was then covered and the system activated. If the mouse passed through the barrier to the dark compartment and broke the photocell beam within 180 seconds, the trap door dropped to block escape to the light compartment and an electric shock was administered at an intensity of 0.4 milliamps for three seconds. The animal was then immediately removed from the dark compartment and placed in its home cage. If the animal failed to break the photocell beam within 180 seconds, it was discarded. The latency is seconds for each mouse was recorded.

Twenty-four hours later, the animals were again tested in the same apparatus except that no injections were made and the mice did not receive a shock. The test day latency in seconds for each animal was recorded and the animals were then discarded.

The high degree of variability (due to season of the year, housing conditions, and handling) found in one trial passive avoidance paradigm is well known. To control for this fact, individual cutoff (CO) values were determined for each test, compensating for interest variability. Additionally, it was found that 5 to 7% of the mice in the scopolamine/vehicle control groups were insensitive to scopolamine at 3 mg/kg, sc. Thus, the CO value was defined as the second highest latency time in the control group to more accurately reflect the 1/15 expected control responders in each test group. Experiments with a variety of standards repeated under a number of environmental conditions led to the development of the following empirical criteria: for a valid test, the CO value had to be less than 120 sec and the vehicle/vehicle control group had to have at least 5/15 animals with latencies greater than CO. For a compound to be considered active the scopolamine/compound group had to have at least 3/15 mice with latencies greater than CO.

The results of the dark avoidance test are expressed as the number of animals per group (%) in which this scopolamine induced memory deficit is blocked as measured by an increase in the latency period. Relief of memory dysfunction activity for representative compounds of the present invention is presented in the Table.

TABLE

| Compound | Dose (mg/kg, sc) | Percent of Animals with Scopolamine Induced Memory Deficit Reversal |
| --- | --- | --- |
| 5-Methylpyrido[3,4-b]-[1,4]benzoxazepin-6(5)-one hydrochloride | 2.5 | 22 |
| 5,6-Dihydro-5-methylpyrido-[3,4-b][1,4]benzoxazepine maleate | 1.25 | 20 |
| 5-(2-Dimethylaminoethyl)-pyrido[3,4-b][1,4]benzoxazepin-6(5H)-one dimaleate | 2.5 | 30 |
| 6-(4-Methyl-1-piperazinyl)-pyrido[3,4-b][1,4]benzoxazepine | 0.63 | 20 |

Scopolamine induced memory deficit reversal is achieved when the present pyridobenzoxazepines are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

Additional pyridobenzoxazepines of the present invention include:
a. 9-Methylpyrido]3,4-b][1,4]benzoxazepin-6(5H)-one;
b. 10-Chloropyrido[3,4-b][1,4]benzoxazepin-6(5)-one;
c. 5,6-Dihydropyrido-11-methoxy[3,4-b][1,4]benzoxazepin-6(5H)-one; and
d. b 5,6-Dihydropyrido-8-trifluoromethyl[3,4-b][1,4]benzoxazepin-6(5H)-one Effective amounts of the compounds of the invention may be administered to a subject by any of various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience of crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid, oxalic acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

Pyrido[3,4-b][1,4]benzoxazepin-6(5H)-one

A solution of 2-(4-amino-3-pyridyloxy)benzoic acid methyl ester (7.5 g) in dimethylformamide (25 ml) was slowly added to a suspension of sodium hydride (60%) oil dispersion, 1.4 g), washed with hexanes, in dimethylformamide (5 ml). After one hr, the reaction mixture was stirred with ice-water and extracted with chloroform. The organic extract was washed with water, saturated sodium chloride solution, dried over anhydrous magnesium sulfate; filtered, and evaporated to 5.5 g (84%) of product. Recrystallization from absolute ethanol gave the analytical sample, mp 253°–254° C.

Analysis: Calculated for $C_{12}H_8N_2O_2$: 67.92% C; 3.80% H; 13.20% N. Found: 67.66% C; 3.88% H; 13.21% N.

EXAMPLE 2

5-Methylpyridol[3,4-b][1,4]benzoxazepin-6(5H)-one hydrochloride

A solution of pyridol[3,4-b][1,4]benzoxazepin-6-(5H)-one (4.5 g) in dimethylformamide (45 ml) was slowly added to sodium hydride (60% oil dispersion, 0.9 g,), washed with hexanes, in dimethylformamide (6 ml), cooled with ice. After the evolution of hydrogen ceased, a solution of dimethyl sulfate (2.9 g) in dimethylformamide (6 ml) was added. After one hr, the reaction mixture was stirred with ice-water and extracted with dichloromethane. The organic extract was washed with water and saturated sodium chloride solution, dried over anhydrous magnesium sulfate, filtered, and evaporated. The residue was purified by flash chromatography (silica, ethyl acetate) to give 3.8 g (79%) of product. The product was converted to the hydrochloride salt by treatment with ethereal hydrogen chloride in 2-propanol. The analytical sample had mp 226°–228° C. (dec.).

Analysis: Calculated for $C_{13}H_{10}N_2O_2.HCl$: 59.43% C; 4.22% H; 10.67% N. Found: 59.34% C; 4.28% H; 10.59% N.

EXAMPLE 3

5-(2-Dimethylaminoethyl)pyrido[3,4-b][1,4]benzoxazepin-6(5H)-one dimaleate

A solution of pyrido[3,4-b][1,4]benzoxazepin-6(5H)-one (4 g), in dimethylformamide (50 ml) was slowly added to sodium hydride (60% oil dispersion, 0.8 g), washed with hexanes, in dimethylformamide (5 ml). After evolution of hydrogen ceased, a solution of 2-dimethylaminoethyl chloride (3 g) in dimethylformamide (5 ml) was added. After stirring for one hr at 80° C., the reaction mixture was cooled, stirred with ice-water and extracted with dichloromethane. The organic extract was washed with water and saturated sodium chloride solution, dried over anhydrous magnesium sulfate, filtered, and evaporated. The residue was purified by flash chromatography (silica, 10% methanol in dichloromethane) to give 3.5 g (65%) of product, as an oil. The product was purified by column chromatography (alumina, ether), and was converted to the dimaleate salt by treatment with maleic acid in 2-propanol. Recrystallization from isopropanol and then from ethanol-ether gave the analytical sample, mp 114°–116° C.

ANALYSIS: Calculated for $C_{16}H_{17}N_3O_2.2C_4H_4O_4$: 55.92% C; 4.89% H; 8.15% N. Found: 56.23% C; 5.05% H; 8.20% N.

EXAMPLE 4

5-(3-Dimethylaminopropyl)pyrido[3,4-b][1,4]benzoxazepin-6(5H)-one dihydrochloride A solution of pyrido[3,4-][1,4]benzoxazepin-6(5H)-one (3 g), in dimethylformamide (25 ml) was added to an ice-cooled suspension of sodium hydride (60% oil dispersion, 0.6 g) washed with hexanes, in dimethylformamide (1 ml). After evolution of hydrogen ceased, a solution of 3-dimethylaminopropyl chloride (3 g) in dimethylformamide (5 ml) was added. After stirring thirty minutes at 80° C., the reaction mixture was cooled, stirred with ice-water and extracted with dichloromethane. The organic extract was washed with water and saturated sodium chloride solution, dried over anhydrous magnesium sulfate, filtered, and evaporated. The residue was purified by flash chromatography (silica, 10% methanol in dichloromethane) to give 3 g (71%) of product, as an oil. The product was converted to the dihydrochloride salt by treatment with ethereal hydrogen chloride in 2-propanol. Recrystallization from 2-propanol gave the analytical sample, mp 244°–246° C. (dec.).

ANALYSIS: Calculated for $C_{17}H_{19}N_3O_2.2HCl$: 55.14% C; 5.72% H; 11.35% N. Found: 54.76% C; 5.83% H; 11.17% N.

EXAMPLE 5

5-(2-Propynyl)pyrido[3,4-b][1,4]benzoxazepin-6(5H)-one hydrochloride

A solution of pyrido[3,4-b][1,4]benzoxazepin-6(5H)-one (6 g) in dimethylformamide (75 ml) was slowly added to an ice-cooled suspension of sodium hydride (60% oil dispersion, 1.2 g) washed with hexanes, in dimethylformamide (5 ml). After evolution of hydrogen ceased, a solution of propargyl bromide (80 wt. % in toluene, 4.6 g) in dimethylformamide (10 ml) was added. After one hr, the reaction mixture was stirred withy ice-water and extracted with dichloromethane. The organic extract was filtered, washed with water and saturated sodium chloride solution, dried over anhydrous magnesium sulfate, filtered and evaporated. The residue was purified by flash chromatography (silica 5%, ethyl acetate in dichloromethane) to give 5.1 g (72%) of product, mp 156°–158° C. The hydrochloride salt was prepared by treatment of the product with ethereal hydrogen chloride in 2-propanol. Recrystallization from 2-propanol, and then ethanol-ether gave the analytical sample, mp 212°–214° C. (dec.).

ANALYSIS: Calculated for $C_{15}H_{10}N_2O_2.HCl$: 62.83% C; 3.87% H; 9.77% N. Found: 63.25% C; 3.81% H; 9.91% N.

EXAMPLE 6

5-[4-Pyrrolidin-1-yl)-2-butynyl]pyrido[3,4-b][1,4]benzoxazepin-6(5H)-one dihydrochloride A mixture of 5-(2-propynyl)pyrido[3,4-b][1,4]benzoxazepin-6(5H)-one (2.6g), pyrrolidone (0.8 g), paraformaldehyde (2.5 g) and cuprous chloride (0.1 g) in dioxane (25 ml) was warmed for 30 mins on a steam bath, cooled, filtered and evaporated. The residue was purified by flash chromatography (silica, 10% methanol in dichloromethane) and the appropriate fractions were combined and converted to the dihydrochloride salt by treatment with ethereal hydrogen chloride in 2-propanol. Recrystallization from 2-propanol gave 2.1 g (50%) of product, mp 205°–207° C. (dec.).

ANALYSIS: Calculated for $C_{20}H_{19}N_3O_2.2HCl$: 59.12% C; 5.21% H; 10.34% N. Found: 58.97% C; 5.16% H; 10.45% N.

EXAMPLE 7

5,6-Dihydropyrido[3,4-b][1,4]benzoxazepine maleate

To a suspension of pyrido[3,4-b][1,4]benzoxazepin-6(5H)-one (5.5 g) in tetrahydrofuran (100 ml) was slowly added lithium aluminum hydride (1M in tetrahydrofuran, 33 ml). After one hr, the solution was diluted with 500 ml ether and quenched with saturated ammonium chloride solution. The layers were separated and the organic phase was washed with water and saturated sodium chloride solution, dried over anhydrous magnesium sulfate, filtered, and evaporated. The residue was purified by flash chromatography (silica, 10% methanol in dichloromethane) to give 4.4 g (86%) of product. The product was converted to the maleate salt by treatment with maleic acid in 2-propanol. Recrystallization from 2-propanol and then ethanol-ether gave the analytical sample, mp 157°–159° C. (dec).

ANALYSIS Calculated for $C_{12}H_{10}N_2O.C_4H_4O_4$: 61.14% C; 4.49% H; 8.92% N. Found: 61.15% C; 4.37% H; 8.83% N.

EXAMPLE 8

5-Acetyl-5,6-dihydropyrido[3,4-b][1,4]benzoxazepine hydrochloride

A solution of 5,6-dihydropyrido[3,4-b][1,4]benzoxazepine (2.8 g) in acetic anhydride (15 ml) was stirred for one hr at ambient temperature. The reaction mixture was poured over ice, basified with sodium carbonate solution and extracted with ether. The organic extract was washed with water, saturated sodium chloride solution, dried over anhydrous magnesium sulfate, filtered, and evaporated. The residue was purified by flash chromatography (silica, ethyl acetate) to give 3 g (88%) of producet, mp 130°–133° C. The product was converted to the hydrochloride salt by treatment with ethereal hydrogen chloride in ethanol. Recrystallization from ethanol-ether gave the analytical sample, mp 225°–227° C. (dec).

ANALYSIS: Calculated for $C_{14}H_{12}N_2O_2.HCl$: 60.76% C; 4.74% H; 10.13% N. Found: 60.69% C; 4.90% H; 10.10% N.

EXAMPLE 9

5,6-Dihydro-5-methylpyrido[3,4-b][1,4]benzoxazepine maleate

A solution of 5,6-dihydro[3,4-b][1,4]benzoxazepine (5.5 g) in dimethylformamide (30 ml) was added to an ice-cooled suspension of sodium hydride (60% oil dispersion, 1.3 g), washed with hexanes, in dimethylformamide (10 ml). After evolution of hydrogen ceased, a solution of dimethyl sulfate (3.8 g) in dimethylformamide (10 ml) was added. After one hr, the reaction mixture was stirred with ice-water and was extracted with dichloromethane. The organic extract was washed with water and saturated sodium chloride solution, dried over anhydrous magnesium sulfate, filtered and evaporated. The residue was purified by flash chromatography (silica, ethyl acetate) to give 3.2 g (52%) of product, as an oil. The product was converted to the maleate salt by treatment with maleic acid in 2-propanol. Recrystallization from 2-propanol and then ethanol-ether gave the analytical sample, mp 127°–129° C.

ANALYSIS: Calculated for $C_{13}H_{12}N_2O \cdot C_4H_4O_4$: 62.19% C; 4.91% H; 8.53% N. Found: 6.190% C; 4.86% H; 8.48% N.

EXAMPLE 10

6-(4-Methyl-1-piperazinyl)pyrido[3,4-b][1,4]benzoxazepine

A suspension of pyrido[3,4-b][1,4]benzoxazepin-6(5H)-one (5 g) in phosphorus oxychloride (75 ml) was refluxed for five hrs and then evaporated. A solution of N-methylpiperazine (25 g) in toluene (200 ml) was slowly added, and the solution was stirred at 80° C. for one hr, cooled, stirred with water, basified with sodium carbonate solution, and extracted with dichloromethane. The organic extract was washed with water and saturated sodium chloride solution, dried over anhydrous magnesium sulfate, filtered, and evaporated. The residue was purified by high performance liquid chromatography (silica, 5% methanol/dichloromethane). The appropriate fractions were collected, evaporated, and the residues were recrystallized twice from 10% ether-hexane to give 3.2 g (49%) of product, mp 124°–125° C.

ANALYSIS: Calculated for $C_{17}H_{18}N_4O$: 69.36% C; 6.16% H; 19.04% N. Found: 69.37% C; 6.17% H; 18.93% N.

We claim:

1. A compound of the formula

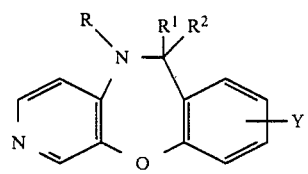

wherein R is hydrogen, loweralkyl, loweralkanoyl, a group of the formula $(CH_2)_m NR^3 R^4$ wherein $R^3$ and $R^4$ are loweralkyl and m is 2 or 3, a group of the formula $CH_2C \equiv CH$, a group of the formula

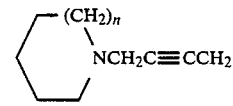

wherein n is 0 or 1; $R^1$ and $R^2$ are hydrogen; $R^1$ and $R^2$ taken together with the carbon atom to which they are attached form a group of the formula C=O; Y is hydrogen, loweralkyol, halogen, loweralkoxy, or trifluoromethy; an optical isomer thereof; or a pharmaceutically acceptable salt thereof.

2. A compound of claim 1 wherein $R^1$ and $R^2$ taken together with the carbon atom to which they are attached form a group of the formula C=O.

3. A compound of claim 1 wherein $R^1$ and $R^2$ are hydrogen.

4. A compound of claim 2 which is pyrido[3,4-][1,4]benzoxazepin-6(5H)-one.

5. The compound of claim 2 which is 5-methylpyrido[3,4-][1,4]benzoxazepin-6(5H)-one.

6. The compound of claim 2 which is 5-(2-dimethylaminoethyl)pyrido[3,4-b][1,4]benzoxazepin-6(5H)-one.

REACTION SCHEME

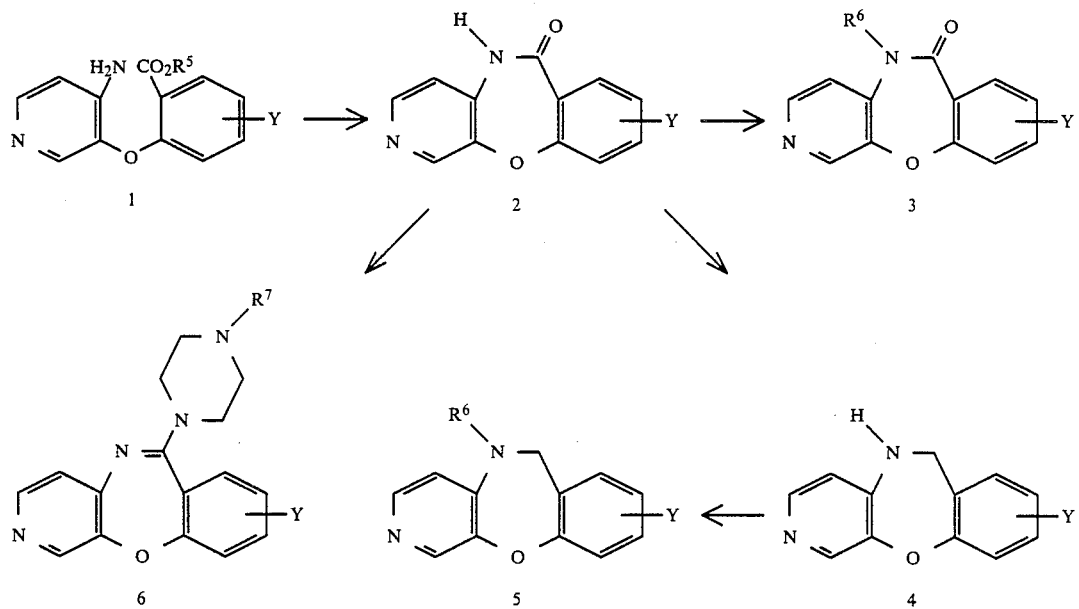

wherein $R^5$, $R^6$, $R^7$, and Y are as hereinbeforedescribed

7. The compound of claim 2 which is 5-(3-dimethylaminopropyl)pyrido[3,4-b][1,4]benzoxazepin-6(5H)-one.

8. The compound of claim 2 which is 5-(2-propynyl)-pyrido[3,4-b][1,4]benzoxazepin-6(5H)-one.

9. The compound of claim 2 which is 5-[4-pyrrolidin-1-yl)-2-butynyl]pyrido[3,4-b][1,4]benzoxazepin-6(5H)-one.

10. The compound of claim 3 which is 5,6-dihydropyrido[3,4-b][1,4]benzoxazepine.

11. The compound of claim 3 which is 5-acetyl-5,6-dihydropyrido[3,4-b][1,4]benzoxazepine.

12. The compound of claim 3 which is 5,6-dihydro-5-methylpyrido[3,4-b][1,4]benzoxazepine.

13. A method of treating depression in mammals comprising administering to a mammal requiring depression treatment, a depression treating amount of a compound of claim 1.

14. A method of alleviating pain in mammals comprising administering to a mammal requiring pain alleviation, a pain alleviating amount of a compound of claim 1.

15. A method of relieving memory dysfunction in mammals comprising administering to a mammal requiring memory dysfunction relief, a memory dysfunction relieving effective amount of a compound of claim 1.

16. A depression treating composition comprising an adjuvant and as the active ingredient, a depression treating effective amount of a compound of claim 1.

17. A pain alleviating composition comprising an adjuvant and as the active ingredient, a pain alleviating effective amount of a compound of claim 1.

18. A memory dysfunction relieving composition comprising an adjuvant and as the active ingredient, a memory dysfunction relieving effective amount of a compound of claim 1.

19. A process for the preparation of a compound of the formula

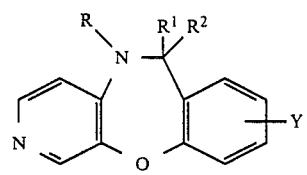

wherein R is hydrogen; $R^1$ and $R^2$ taken together with the carbon atom to which they are attached form a group of the formula C=O; Y is hydrogen, loweralkyl, halogen, loweralkoxy, or trifluoromethyl, which comprises contacting a compound of the formula

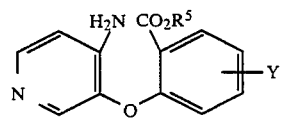

wherein $R^5$ is loweralkyl and Y is as above with a base.

20. The process of claim 19 wherein the base is lithium hydride, sodium hydride, or potassium hydride.

21. The process of claim 20 wherein the base is sodium hydride.

22. The process of claim 19 wherein a solvent is employed.

23. The process of claim 22 wherein the solvent is a dipolar aprotic solvent.

24. The process of claim 23 wherein the dipolar aprotic solvent is dimethylformamide, dimethylacetamide, dimethylsulfoxide, or hexamethylphosphoramide.

25. The process of claim 24 wherein the dipolar aprotic solvent is dimethylformamide.

26. 6-(4-Methyl-1-piperazinyl)pyrido[3,4-b][1,4]benzoxazepine.

* * * * *